United States Patent [19]

Farha, Jr. et al.

[11] 3,957,688

[45] May 18, 1976

[54] CATALYTIC DEHYDROGENATION PROCESS

[75] Inventors: Floyd Farha, Jr.; Lewis E. Drehman, both of Bartlesville, Okla.

[73] Assignee: Phillips Petroleum Company, Bartlesville, Okla.

[22] Filed: Nov. 15, 1973

[21] Appl. No.: 415,943

[52] U.S. Cl............................ 252/455 R; 252/459; 252/460; 252/466 J; 252/466 PT; 252/476
[51] Int. Cl.².......................................... B01J 29/06
[58] Field of Search............... 252/455 R, 459, 460, 252/466 PT, 466 J, 476

[56] References Cited
UNITED STATES PATENTS

| | | | |
|---|---|---|---|
| 2,662,861 | 12/1953 | Riblett et al. | 252/455 R |
| 2,777,805 | 1/1957 | Lefrancois et al. | 252/460 X |
| 3,156,735 | 11/1964 | Armstrong | 252/460 X |
| 3,670,044 | 6/1972 | Drehman et al. | 252/460 X |
| 3,692,701 | 9/1972 | Box | 252/466 PT |
| 3,789,020 | 1/1974 | Carter et al. | 252/460 X |

*Primary Examiner*—Paul F. Shaver

[57] ABSTRACT

Dehydrogenatable organic compounds diluted with steam, are dehydrogenated in the absence of free oxygen at high conversion and selectivity to less saturated compounds with a catalyst composite consisting essentially of one or more metals selected from the group consisting of Ni, Pd, Pt, Ir and Os, tin and a metal selected from the group consisting of gold and silver deposited on a support such as alumina, silica or a Group II aluminate spinel.

12 Claims, No Drawings

CATALYTIC DEHYDROGENATION PROCESS

This invention relates to the catalytic dehydrogenation of organic compounds. In one aspect, it relates to dehydrogenation processes. In another aspect it relates to dehydrogenation catalysts.

The dehydrogenation of organic compounds is well known. While non-catalytic thermal dehydrogenation of organic compounds is known, the use of such methods is limited because of the extensive undesirable side reactions which take place. Thus, a great number of catalytic processes have been developed in order to minimize side reaction activity and improve conversion and selectivity to desired products. Materials which have been proposed as dehydrogenation catalytic agents include Group VIII metal and metal compounds reducible to the metal, e.g. noble metal compounds. Generally, such catalytic agents as the Group VIII metal compounds have been proposed in combination or association with a carrier or support material such as alumina, silica, and the like. The Group VIII metal compound-containing catalytic agents are characterized by high dehydrogenation activity and selectivity. Such materials, however, are subject to deactivation particularly by coke laydown, and can lose their activity very quickly, e.g., in a matter of minutes. Hence, although the selectivity and activity of the Group VIII metal, particularly the noble metals, catalytic agents in dehydrogenation processes are excellent, the cost of such agents in relation to their catalytic activity and the need for frequent regeneration have inhibited their acceptance in commercial dehydrogenation applications.

It is known that the activity and useful life of such catalysts can be increased and extended by incorporating tin into such catalysts. While overcoming to some extent the drawbacks of the Group VIII metal-containing catalysts per se, such catalysts still exhibit certain deficiencies. For example, platinum/tin/zinc aluminate catalysts are highly active and selective for dehydrogenation and dehydrocyclization of paraffins. However, they lose activity during use and require regeneration at periodic intervals depending upon the feed used.

It is, therefore, an object of this invention to provide an improved dehydrogenation process.

It is an object of this invention to provide improved dehydrogenation catalyst systems.

Other aspects and objects will be apparent to those skilled in the art from the following disclosure, example, and appended claims.

In accordance with this invention, it has been discovered that the activity and stability of tin-promoted nickel-, palladium-, platinum-, iridium-, and osmium-containing catalysts are unexpectedly improved by modifying such catalysts with a metal selected from the group consisting of gold and silver.

The finished catalyst compositions are useful in dehydrogenation processes wherein a steam-diluted dehydrogenatable organic compound is contacted with such catalysts in the vapor phase in the substantial absence of free oxygen.

The novel catalysts of this invention consist essentially of at least one Group VIII metal or metal compound capable of reduction in combination with tin and a co-promoting metal selected from the group consisting of gold and silver. The Group VIII metals include nickel, palladium, platinum, iridium and osmium, including compounds of such metals which are capable of reduction, e.g., platinic chloride, chloroplatinic acid, ammonium chloroplatinate and the like and various coordination compounds such as platinum diamine oxalate, platinum hexammine dihydroxide and the like, and mixtures thereof. The Group VIII metal content of the catalysts is in the approximate range of 0.1 to 5 weight percent of the support.

In addition to the Group VIII metals, the catalyst composition contains tin as a first co-promoter metal. The amount of tin is in the approximate range of 0.01 to 5 weight percent of the support. The tin component can be deposited with the Group VIII metal component upon the catalytic carrier of the invention, separately or together by any manner known in the art such as by deposition from aqueous and non-aqueous solutions of tin halides, nitrates, oxalates, acetates, oxides, hydroxides and the like.

In addition to the Group VIII metal and tin, the catalyst composition contains a second co-promoter metal or metal compound which can be gold or silver or mixtures thereof. The amount of the second co-promoter metal is in the approximate range of 0.1 to 5 weight percent of the support. Suitable gold and silver compounds include: auric chloride, auric sulfate, aurous chloride, tetrachloroauric acid, silver nitrate, silver acetate, silver cyanide and the like.

In a preferred embodiment, the amount of Group VIII metal, as defined above, is in the approximate range of 0.1 to 1 weight percent. The amount of tin is in the approximate range of 0.1 to 2 weight percent and the amount of co-promoter metal is in the approximate range of 0.1 to 2 weight percents, all weight percents based upon the weight of final catalyst.

The molar ratio of the Group VIII metal to tin can be in the range of 10:1 to 1:10. The molar ratio of the Group VIII metal to the second co-promoter can be in the range of 10 to 1:10. In a presently preferred embodiment the Group VIII metal to tin ratio is in the approximate range of 2:1 to 1:5 and the Group VIII metal to second co-promoter ratio is in the approximate range of 2:1 to 1:3. In a more preferred embodiment the Group VIII metal to tin ratio is about 1:3 and the Group VIII metal to second co-promoter ratio is about 1:1.

The carrier material which is employed in the preparation of the catalyst of this invention include alumina, silica, magnesia, zirconia, alumino-silicates, Group II aluminate spinels and mixtures thereof. In a preferred embodiment the support material is a Group II aluminate spinel, particularly zinc aluminate spinel.

The catalytic materials of this invention can be prepared by any means known in the art, e.g., by coprecipitation, by impregnation, by mixing dry powders, by mixing aqueous and non-aqueous slurries and pastes and the like.

During the dehydrogenation reaction, the catalyst which can be in any suitable form such as granules, pills, pellets, spheres, and the like, will slowly lose some activity and will periodically require a regeneration by conventional means. In one regeneration method, the feedstock is cut off and the catalyst is treated with steam-diluted air such that the oxygen content of the mixture is about 1–5 mol percent. The regeneration treatment can be carried out at temperatures and pressures within the dehydrogenation operating range for about 15 to 60 minutes.

The catalytic dehydrogenation processes of this invention are effected at temperatures within the range of about 750° to about 1250°F, preferably in the range of 1000° to 1100°F, with the exact conditions being dependent upon the feedstock and product desired. Pressures are generally in the range of about 0 to 500 p.s.i.g., and the space velocity is within the range of 200 to 10,000 volumes of feedstock per volume of catalyst per hour. The reactions of the invention are carried out in the vapor phase in the presence of steam and in the absence of oxygen at molar ratios of steam to organic feestock in the range of 0.5–30:1, preferably 2.5–15:1.

The processes of this invention are particularly well suited for the dehydrogenation of various dehydrogenatable organic compounds containing at least one

grouping, i.e., adjacent C atoms singly bonded to each other and each attached to at least one hydrogen atom. In addition to carbon and hydrogen, these compounds can also contain nitrogen. Such compounds can contain from 2 to 12 carbon atoms. Among the class of organic compounds which can be treated according to the processes of this invention are alkanes, cycloalkanes, alkyl aromatic compounds, alkenes, alkyl-substituted pyridines and the like. The catalyst composition of this invention is particularly effective for the dehydrogenation of paraffins having from 2 to 12 carbon atoms.

The catalysts of this invention employing gold as co-promoter are particularly effective in processes using a fixed bed catalytic reactor. The catalysts of this invention employing silver as co-promoter are particularly effective in moving bed dehydrogenation processes.

The following examples illustrate the invention.

EXAMPLE I

Tin-Containing Support

A slurry consisting of distilled water, finely divided alumina, finely divided reagent grade zinc oxide and finely divided reagent stannic oxide was ball milled for one hour to obtain an intimate mixture. The slurry was dried overnight at 200°–220°F in a forced draft oven. The resulting dry cake was crushed, sieved to remove coarse particles and the powder was compounded with 8 weight percent of a polyethylene lubricant. The mixture was formed into ⅛-inch pellets and calcined in air in a muffle furnace which was programmed as follows: 2 hours at 800°F, 2 hours at 1100°F and 3 hours at 1850°F. After cooling, the calcined pellets were crushed and sieved to obtain 16–20 mesh particles. The thus prepared support had a surface area of 12.0 square meters per gram, a pore volume of 0.33 cc per gram and an apparent bulk density of 0.96 gram per cc. The support contained 39 weight percent zinc, 26.8 weight percent aluminum, 1.0 weight percent tin and 33.2 weight percent combined oxygen.

EXAMPLE II

Preparation of Catalysts

Catalyst A: A portion of the tin-containing catalyst support of Example I was impregnated with platinum from an aqueous solution of chloroplatinic acid to form a catalyst composition containing 0.6 weight percent platinum based on the weight of the final catalyst. The mixture was dried 3 hours at 230°F and calcined 3 hours at 1100°F.

Catalyst B: A portion of the tin-containing catalyst support of Example I was impregnated with platinum and gold from an aqueous solution of chloroplatinic acid and tetrachloroauric acid to form a catalyst composition containing 0.6 weight percent each of platinum and gold based on the weight of the final catalyst. This mixture was dried 3 hours at 230°F and calcined 3 hours at 1100°F.

Catalyst C: A portion of the tin-containing catalyst support of Example I was impregnated with silver from an aqueous solution of silver nitrate to form a catalyst composition containing 0.4 weight percent of silver based on the weight of the final catalyst. The mixture was dried, then impregnated with an aqueous solution of chloroplatinic acid sufficient to give 0.6 weight percent platinum based on the weight of the final catalyst. The mixture was dried 3 hours at 220°F and calcined 3 hours at 1050°F.

Catalyst D: A portion of the tin-containing catalyst support of Example I was impregnated with copper and platinum from an aqueous solution of cupric nitrate and chloroplatinic acid sufficient to give 0.2 weight percent copper and 0.6 weight percent platinum based on the weight of the final catalyst. The mixture was dried 3 hours at 220°F and calcined 3 hours at 1050°F.

EXAMPLE III

Dehydrogenation runs were conducted to determine the effects of gold and silver as co-promoters for the reference catalyst A. n-Butane was dehydrogenated at 1100°E and 100 p.s.i.g. in the presence of 9–10 mols of steam per mol of n-butane and in the substantial absence of free oxygen. In each run, 1.4 cc of catalyst was used. The processes were conducted in a cyclic, continuous flow manner with an intermediate air regeneration of the catalyst. Each cycle consisted of a dehydrogenation step of 11.5 hours at the recited conditions, followed by a catalyst regeneration step of 30 minutes effected at process conditions. Regeneration was accomplished by shutting off the feed without disturbing the steam injection rate for 5 minutes, then admitting sufficient air with the steam to provide about 2 mol percent of oxygen for 20 minutes, followed by another 5-minute purge with steam only. The results shown in Table I are the average at at least 3 such cycles.

The reactor effluent was analyzed by means of gasliquid chromatography at the times indicated. Total conversion of the n-butane feed is in terms of mol percent. Selectivity is given in terms of the percentage of total products formed converted into butenes and butadiene. Results are given in Table I.

In each of the runs given in Table I, the mol ratio of Sn:Pt is 2.74:1.

Table I

| Run No. | 1 | 2 | 3 | 4 |
|---|---|---|---|---|
| Catalyst | A | B | C | D |

Table I-continued

| Co-promoter | none | Au | Ag | Cu |
|---|---|---|---|---|
| weight percent | — | 0.6 | 0.4 | 0.2 |
| mol/mol pt. | — | 0.99 | 1.21 | 1.02 |
| n-Butane GHSV | 7070 | 6410 | 6460 | 6600 |
| 1 Hour on Stream | | | | |
| conversion, % | 32.5 | 34.0 | 39.4 | 30.8 |
| selectivity, % | 94.6 | 95.1 | 95.2 | 94.4 |
| rate constant, K$^{(a)}$ | 11,500 | 11,800 | 13,500 | 9540 |
| 6 Hours on Stream | | | | |
| conversion, % | 21.3 | 23.2 | 19.5 | 10.6 |
| selectivity, % | 92.2 | 94.3 | 93.3 | 88.5 |
| K | 5000 | 5900 | 4300 | 1920 |
| k$^{(b)}$ | 0.44 | 0.50 | 0.32 | 0.20 |
| 11 Hours on Stream | | | | |
| conversion, % | 15.0 | 17.2 | 6.7 | 4.2 |
| selectivity, % | 87.9 | 93.5 | 83.7 | 74.5 |
| K | 2850 | 3700 | 1070 | 550 |
| k | 0.25 | 0.31 | 0.08 | 0.06 |
| Rate of Decline in Activity,$^{(c)}$ %/hr. | | | | |
| 1–6 hours on stream | 15.3 | 13.0 | 20.5 | 27.4 |
| 1–11 hours on stream | 13.0 | 10.9 | 22.4 | 24.8 |
| Coke Rate, in Mmols/hr. | 0.49 | 0.49 | 0.14 | 0.16 |
| K$_o{}^{(d)}$ | 14,500 | 14,500 | 15,800 | 13,000 |

$^{(a)}$dehydrogenation rate constant.

$$K = \frac{(GHSV)(conversion)(selectivity)}{(equilibrium\ conversion)(equilibrium\ conversion - conversion \times selectivity)}$$

$^{(b)}$relative rate constant.

$$k = \frac{K\ at\ 6\ or\ 11\ hours}{K\ at\ 1\ hour}$$

$^{(c)}K = (1-r)^{(t-1)}$, where r is the rate of decline and t is the number of hours on stream.

$^{(d)}$K at time zero. Determined from curves of K vs. time.

Examination of the above data reveals that the reference catalyst, A, while very active and selective for dehydrogenating n-butane, loses such activity rapidly.

The gold co-promoted catalyst exhibits increased activity and slower rate of deactivation as compared to the reference catalyst.

The silver co-promoted catalyst exhibits enhanced activity, as compared to the reference catalyst, for more than 1 hour but less than 6 hours. In view of its initial activity, the catalyst appears to be well suited for moving bed reactor applications wherein the catalyst briefly contacts the feedstock and is then removed and regenerated for reuse.

Copper is shown not to be a suitable copromoter for the reference catalyst.

Reasonable variations and modifications are possible within the scope of this disclosure without departing from the scope and spirit thereof.

I claim:

1. A catalyst composition suitable for the dehydrogenation of a dehydrogenatable organic compound having from 2 to 12 carbon atoms per molecule in the presence of steam and in the absence of free oxygen consisting essentially of:
   a. from about 0.1 to about 5 weight percent of a metal selected from the group consisting of nickel, palladium, platinum, iridium, osmium and mixtures thereof;
   b. from about 0.01 to about 5 weight percent of tin; and
   c. from about 0.1 to 5 weight percent of a metal selected from the group consisting of gold and silver and mixtures thereof; each of said (a), (b) and (c) being supported on a support selected from the group consisting of alumina, silica, magnesia, zirconia, alumino-silicates, Group II aluminate spinels and mixtures thereof.

2. The composition of claim 1 wherein the mol ratio of said metal (a) to said tin is in the range of 10:1 to 1:10 and the ratio of said metal (a) to said metal (c) is in the range of 10:1 to 1:10.

3. The composition of claim 2 wherein said metal (a) is platinum.

4. The composition of claim 3 wherein said metal (c) is gold.

5. The composition of claim 3 wherein said metal (c) is silver.

6. The composition of claim 3 wherein the mol ratio Pt:Sn: (c) is approximately 1:3:1.

7. The composition of claim 5 wherein said support is zinc aluminate spinel.

8. The composition of claim 1 wherein said metal (a) is present in an amount ranging from 0.1 to 1 weight percent; said tin is present in an amount ranging from 0.1 to 2 weight percent and said metal (c) is present in an amount ranging from 0.1 to 2 weight percent.

9. The composition of claim 1 wherein the mol ratio of said metal (a) to said tin is in the range of 2:1 to 1:5 and the mol ratio of said metal (a) to said metal (c) is in the range of 2:1 to 1:3.

10. The composition of claim 1 wherein the mol ratio of said metal (a) to said tin is about 1:3 and the mol ratio of said metal (a) to said metal (c) is about 1:1.

11. The composition of claim 4 wherein the amount of said platinum is 0.6 weight percent, the amount of said tin is 1.0 weight percent and the amount of said gold is 0.6 weight percent.

12. The composition of claim 5 wherein the amount of said platinum is 0.6 weight percent, the amount of said tin is 1.0 weight percent and the amount of said silver is 0.4 weight percent.

* * * * *

UNITED STATES PATENT AND TRADEMARK OFFICE
CERTIFICATE OF CORRECTION

PATENT NO. : 3,957,688
DATED : May 18, 1976
INVENTOR(S) : Floyd Farha, Jr. et al It is certified that error appears in the above—identified patent and that said Letters Patent are hereby corrected as shown below:

Column 5, claim 1, element (c), line 12, after "to", insert --- about ---.

Signed and Sealed this

Thirty-first Day of August 1976

[SEAL]

Attest:

RUTH C. MASON
Attesting Officer

C. MARSHALL DANN
Commissioner of Patents and Trademarks